United States Patent
Sallis

(10) Patent No.: US 9,192,613 B1
(45) Date of Patent: Nov. 24, 2015

(54) TREATMENT METHOD FOR PRIMARY PREMATURE EJACULATION

(71) Applicant: Sapere IP, LLC, Altamonte Springs, FL (US)

(72) Inventor: Ramsay Sallis, St. Peters (AU)

(73) Assignee: Sapere IP, LLC, Altamonte Springs, FL (US)

( * ) Notice: Subject to any disclaimer, the term of this patent is extended or adjusted under 35 U.S.C. 154(b) by 0 days.

(21) Appl. No.: 14/513,794

(22) Filed: Oct. 14, 2014

(51) Int. Cl.
| | |
|---|---|
| *A61K 31/55* | (2006.01) |
| *A61K 31/20* | (2006.01) |
| *A61K 31/135* | (2006.01) |
| *A61K 31/5575* | (2006.01) |
| *A61K 9/00* | (2006.01) |
| *A61B 8/06* | (2006.01) |
| *A61B 8/08* | (2006.01) |
| *A61B 5/00* | (2006.01) |

(52) U.S. Cl.
CPC ........... *A61K 31/5575* (2013.01); *A61B 5/4393* (2013.01); *A61B 5/4839* (2013.01); *A61B 8/06* (2013.01); *A61B 8/488* (2013.01); *A61K 9/006* (2013.01); *A61K 9/0019* (2013.01); *A61K 9/0043* (2013.01); *A61K 9/0056* (2013.01); *A61K 31/135* (2013.01); *A61K 31/20* (2013.01); *A61K 31/55* (2013.01)

(58) Field of Classification Search
CPC ...... A61K 31/55; A61K 31/20; A61K 31/135
USPC .......................................... 514/217, 559, 646
See application file for complete search history.

(56) References Cited

U.S. PATENT DOCUMENTS 7,405,222 B2    7/2008 Sallis et al.

OTHER PUBLICATIONS

Althof et al., "A Double-Blind Crossover Trial of Clomipramine for Rapid Ejaculation in 15 Couples", Journal of Clin Psychiatry, 1995, 56(9),402-407.
Berkovitch et al., "Efficacy of Prilocaine-Lidocaine Cream in the Treatment of Premature Ejaculation", Journal of Urology, 1995, 154, 1360-1361.
Bookstein et al., "Penile Pharmacocavernosography and Cavernosometry in the Evaluation of Impotence", Journal of Urology, 1987, 137(2), 333-337.
Busato et al., "Topical Anaesthetic Use for Treating Premature Ejaculation: A Double-Blind Randomised, Placebo-Controlled Study", BJU International, 2004, 93,1018-1021.
Choi et al., "Clinical Study of SS-Cream in Patients with Lifelong Premature Ejaculation" Urology, 2000, 55, 257-261.
Cossman et al., "Tolerance and Safety of Tramadol Use. Results of International Studies and Data from Drug Surveillance", Drugs, 1997, [53(Suppl. 2), 50-62], Abstract, 1 page.
Drogo et al., "Premature Ejaculation: Guideline on the Pharmacologic Management of Premature Ejaculation", American Urological Association, 1999, 124 pages.
Fein, "Intracavernous Medication for Treatment of Premature Ejaculation", Urology, 1990, 35(4), 301-303.
Feldman et al., "Impotence and Its Medical and Psychosocial Correlates: Results of the Massachusetts Male Aging Study", Journal of Urology, 1994, 151, 54-61.
Godpodinoff, "Premature Ejaculation: Clinical Subgroups and Etiology", Journal of Sex Marital Therapy, 1989, 15(2), 130-134.
Kim et al., "Efficacy and Safety of Fluoxetine, Sertraline and Clomipramine in Patients with Premature Ejaculation: A Double-Blind, Placebo Controlled Study", Journal of Urology, 1998, 159(2), 425-427.
Laumann et al., "Sexual Dysfunction in the United States: Prevalence and Predictors", JAMA, 1999, 281(6), 9 pages.
Montague et al., "AUA Guideline on the Pharmacologic Management of Premature Ejaculation", Journal of Urology. 2004, 172, 290-294.
Montorsi, "Prevalence of Premature Ejaculation: Global and Regional Perspective", Journal Sex Med, 2005, Supp 2, 96-102.
Namavar et al., "Removal of Foreskin Remnants in Circumcised Adults for Treatment of Premature Ejaculation", Urol Annals, 2011, 3(2), 87-92.
Palmer et al., "Premature Ejaculation: A Clinical Update", Med. J. Aust., 2008, 188(11), 662-666.
"Premature Ejaculation: Definition", International Society for Sexual Medicine (ISSM), http://www.issm.info/education-for-all/featured-education, 2014, 4 pages.
Porst, "The Rationale for Prostaglandin E1 in Erectile Failure: A Survey of Worldwide Experience", Journal of Urology, 1996, 155, 802-815.
Salem et al., "Tramadol HCL Has Promise in On-Demand Use to Treat Premature Ejaculation", J Sex Med., 2008, 5(1), 188-193.
Strassberg et al., "Clomipramine in the Treatment of Rapid (Premature) Ejaculation", J. Sex Marital Ther., 1999, 25(2), 89-101.
Waldinger et al., "Premature Ejaculation and Serotonergic Antidepressants-Induced Delayed Ejaculation: The Involvement of the Serotonergic System", Behav Brain Res., 1998, 92,111-118.
Wong et al., "The Use of Tramadol "On-Demand" for Premature Ejaculation: A Systematic Review", Urology, 2013, 81(1), 98-103.
Xin et al., "Penile Sensitivity in Patients With Primary Premature Ejaculation", Journal of Urology, 1996, 156(3), 979-981.

*Primary Examiner* — Raymond Henley, III
(74) *Attorney, Agent, or Firm* — Baker & Hostetler LLP

(57) ABSTRACT

This method outlines a process which a patient may follow to find a rapid, safe and effective treatment for the common problem of premature ejaculation. The method progresses through three stages including clinical history, diagnostic testing, and treatment. Treatment of primary premature ejaculation includes assessing the condition of the male to establish that the male has primary premature ejaculation as opposed to secondary premature ejaculation and, if the male is diagnosed as having primary premature ejaculation, identifying a treatment protocol that progresses to a safest and most effective methodology in a shortest number of steps. During treatment, the male is progressed through at least two of the following steps in sequence until a satisfactory delay of ejaculation is achieved: applying a clomipramine sublingual spray, applying a clomipramine nasal spray, applying a troche of clomipramine buccally or sublingually, applying tramadol buccally, and injecting a vasodilator into a corpus cavernosum of the male's penis in an amount sufficient to provoke a lasting erection.

8 Claims, 4 Drawing Sheets

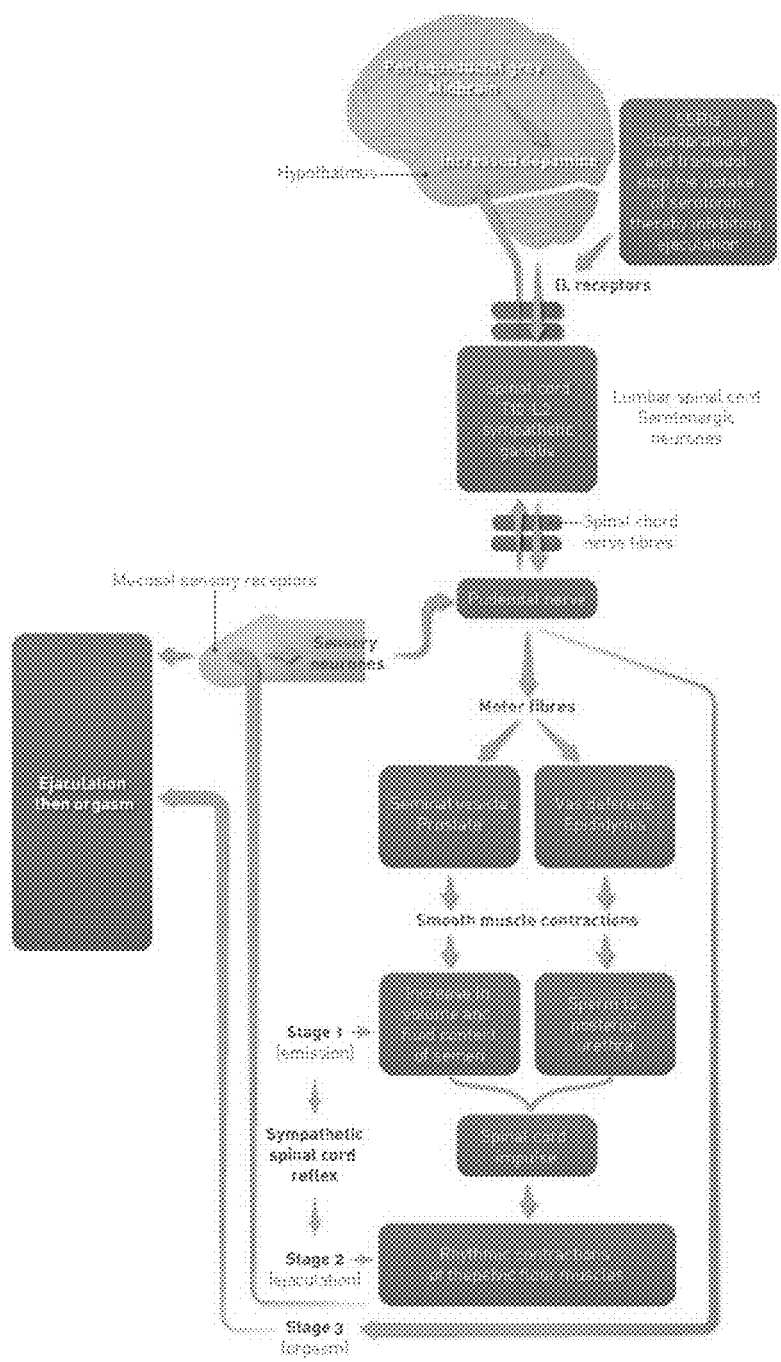
FIGURE 2: Mechanism of ejaculation

TREATMENT METHOD FOR PRIMARY PREMATURE EJACULATION

TECHNICAL FIELD

The invention relates to treatment methods for primary premature ejaculation as distinguished from secondary premature ejaculation and erectile dysfunction

BACKGROUND

There is confusion in the medical profession as to the causes and appropriate treatments for premature ejaculation. In fact, there are a variety of definitions used to describe premature ejaculation. For example, the Diagnostic and Statistical Manual of Mental Disorders (DSM-IV) defines premature ejaculation as ejaculation that occurs without control or as occurring shortly after penetration and before a person wishes it, causing marked distress or interpersonal difficulty (American Psychiatric Association, "Diagnostic and statistical manual of mental disorders," 4th edition, Washington DC: APA 2000). Other definitions of premature ejaculation incorporate a time factor, namely, as ejaculation that occurs always or nearly always before or within about one minute of vaginal penetration, an inability to delay ejaculation on all or nearly all vaginal penetration, and negative personal consequences, such as distress, bother, frustration and/or the avoidance of sexual intimacy (International society for sexual medicine, ISSM, http://www.issm.info/education-for-all/featured-education/). Still other definitions of premature ejaculation involve expectations of the partner, particularly regarding the ability to climax. Masters and Johnson (1970) proposed one of the earliest definitions that focused on the inability to delay ejaculation long enough for women to achieve orgasm fifty percent of the time (Masters W. H. & Johnson V. E., "Human Sexual Inadequacy," Boston: Little, Brown, 1970).

For purposes of the present invention, the inventor have adopted the following definition. Premature ejaculation in accordance with the invention has any one or more of the following characteristics:

i. Ejaculating before or within five minutes after penetration;
ii. Not having control of your ejaculation; and/or
iii. Ejaculating before you have satisfied your partner.

Furthermore, in the context of the invention it is important to differentiate between primary and secondary premature ejaculation. Primary is life long and stems from the very first sexual encounter, while secondary is an acquired form (Godpodinoff M. L., "Premature ejaculation: clinical subgroups and etiology," J Sex Marital Therapy, 1989; 15:130). In the inventors' clinical experience, secondary (acquired) premature ejaculation tends to occur in older patients and is usually the result of an underlying problem of erectile dysfunction. As a result of the inability to sustain an erection, the patient ejaculates more rapidly, learning to climax before the loss of his erection. Hence, the treatment of secondary premature ejaculation falls under the umbrella of treatment for erectile dysfunction. When both premature ejaculation and erectile dysfunction exist concurrently, erectile dysfunction should be treated first (American Urological Association, "Guideline on the pharmacologic management of premature ejaculation," Drogo et al 1999).

In the case of secondary premature ejaculation, that is, premature ejaculation occurring as a result of an erectile problem, treatment involves treating the cause of erectile dysfunction rather than premature ejaculation per se. The treatment of secondary premature ejaculation is not covered herein but distinguishing between the two is important and will be addressed. Methods and compositions for treating erectile dysfunction may be found, for example, in U.S. Pat. No. 7,405,222, to Ramsey Sallis et al. The treatment protocol in accordance with the invention addresses only patients with primary premature ejaculation.

Prevalence of Premature Ejaculation

Premature ejaculation is reported to be the most common sexual dysfunction in men (Montague D. K. et al., "AUA guideline on the pharmacologic management of premature ejaculation," J Urol. 2004; 172:290-294). A study involving 1,234 males showed the following percentages reporting a prevalence of premature ejaculation (Laumann E. O. et al., "Sexual dysfunction in the United States: prevalence and predictors," JAMA 1999; 281:537):

| Age | Total (1234) | Percent (%) |
| --- | --- | --- |
| 18-29 | 121 | 30% |
| 30-39 | 122 | 32% |
| 40-49 | 83 | 28% |
| 50-59 | 55 | 31% |

Some studies show a considerably higher prevalence and results are generally quite variable. This is not surprising given that premature ejaculation is largely self-reported and even now there is little consensus regarding a universal definition. From the inventors' review of the literature, it appears that the more recent the study, the higher the prevalence, which could reflect changing expectations by partners regarding sexual performance.

Causes of Premature Ejaculation

Erectile dysfunction was considered to have principally a psychological etiology up until the early 1990s. Numerous papers quoted incidents in the region of 80:20; 80% psychological and 20% physical. With the advent of more sophisticated diagnostic tools such as the eco-doppler machine for measuring blood flow, the tide has turned, with studies showing an organic detiology in 80-90% of patients (Feldman H. A., McKinlay J. B. et al., "Impotence and its medical and psychosocial correlates: results of the Massachusetts Male Aging Study," J Urol. 1994; 151:54).

The same shift appears to be happening regarding the aetiology of premature ejaculation, from the psychological to the organic. Although, to date, no single etiological theory has universal acceptance, there is a general shift toward the acceptance of the condition as one in which psychologically mediated processes exacerbate an underlying organic component ("Prevalence of premature ejaculation: a global and regional perspective," Montorsi F., J Sex Med; 2005; Supplement 2, page 100).

The traditional psychological approach to premature ejaculation uses sexual conditioning as a factor as introduced by Masters and Johnson in their book *Human Sexual Inadequacy*, Boston: Little, Brown, 1970. For example, patients with premature ejaculation tend to exhibit a nervousness or tension during love making relating to an anxious personality type and stemming from the first sexual encounter.

The most popular organic theory regarding the aetiology of primary premature ejaculation relates to the penile hypersensitivity resulting in a lower ejaculatory threshold (Xin Z. C., Chung W. S. et al., "Penile sensitivity in patients with primary premature ejaculation," J Urol. 1996; 156:979-81). In other words, little physical stimulation causes rapid ejaculation. This could explain why primary premature ejaculation is more common in uncircumcised men and why anesthetic creams or gels are part of many treatment protocols (Namavar M. R. & Robati B., "Removal of foreskin remnants in circumcised adults for treatment of premature ejaculation," Urol Annals 2011, May-August; 3(2):87-92).

In the inventors' clinical experience, men with primary premature ejaculation tend to exhibit both of the following characteristics:

i. nervousness and tension during lovemaking, dating back to the very first sexual encounter; and ii. a hypersensitivity of the glans penis, that is the head of the penis, resulting in a lower ejaculatory threshold.

As noted above, secondary premature ejaculation is premature ejaculation occurring as a result of an erectile problem. Obviously, in such cases treatment involves treating the cause of erectile dysfunction rather than premature ejaculation per se. The treatment of secondary premature ejaculation is not covered herein but distinguishing between the two is important and will be addressed.

Diagnosis

Traditionally, the diagnosis of premature ejaculation has been based on sexual history alone, addressing only the first of the characteristics noted above. Of course, an extensive sexual history should be obtained from all presenting patients and, if agreed upon, their partners may be present. However, such a diagnosis is based on self-reporting. Particularly in this sensitive field of medicine, such self-reporting can often lead to under-reporting. Many men are reluctant to admit to the severity of the problem and its duration, and the effect on their lives, due to embarrassment.

A better diagnosis and treatment protocol is desired to assess premature primary premature ejaculation and distinguish it from secondary premature ejaculation. The invention addresses this significant need in the art by incorporating the traditional history taking with diagnostic testing to provide more tangible parameters.

SUMMARY

The above-mentioned and other needs in the art are addressed by a treatment protocol for primary premature ejaculation in which the condition of the male is first assessed to establish that the male has primary premature ejaculation as opposed to secondary premature ejaculation. Assessing the condition of the male may include using questionnaires to a establish a comprehensive history of the patient's medical condition and sexual history and applying diagnostic tests to the male including Eco-Doppler to measure blood flow of the penis and biothesiometry to determine the sensitivity of the nerves of the penis.

In exemplary embodiments, if the male is diagnosed as having primary premature ejaculation, a treatment protocol is identified that progresses to a safest and most effective methodology in a shortest number of steps by progressing the male through at least two of the following steps in sequence until a satisfactory delay of ejaculation is achieved:

applying a clomipramine sublingual spray in an amount effective to delay ejaculation by the male, applying a clomipramine nasal spray in an amount effective to delay ejaculation by the male, applying a troche of clomipramine buccally or sublingually in an amount effective to delay ejaculation by the male, applying tramadol buccally in an amount effective to delay ejaculation by the male, and injecting a vasodilator into a corpus cavernosum of the male's penis in an amount sufficient to provoke a lasting erection.

In exemplary embodiments, the treatment protocol particularly includes applying an aqueous formulation of clomipramine salt sublingually in a dosage from 4-12 mg based on the male's weight, applying an aqueous formulation of clomipramine salt nasally in a dosage from 4-12 mg based on the male's weight, and applying a combination of clomipramine salt and an amount of an anti-nauseant sufficient to suppress nausea buccally or sublingually in a dosage of 20 mg of clomipramine and 2 mg of the anti-nauseant, determining if an effective delay of ejaculation is achieved, and increasing the dosage of clomipramine and anti-nauseant up to 50 mg and 5 mg, respectively, until an effective delay of ejaculation is achieved. The male is progressed through these dosages until a satisfactory result is achieved.

If no satisfactory result is achieved with various dosages of clomipramine, a troche of tramadol salt is applied buccally in a dosage of 10 mg of tramadol. It is then determined if an effective delay of ejaculation is achieved and, if not, the dosage of tramadol is increased up to 30 mg until an effective delay of ejaculation is achieved.

If no satisfactory result is achieved with various dosages of clomipramine or tramadol, then a solution of Alprostadil is injected in the male's penis in a dosage of 0.25 ml (20 mcg/ml) of Alprostadil. It is then determined if an effective delay of ejaculation is achieved and, if not, the dosage of Alprostadil is increased up to 1 ml until an effective delay of ejaculation is achieved.

It will be appreciated by those skilled in the art that the claimed treatment protocol does not start with the most effective but potentially most adverse treatment; rather, the treatment protocol of the invention instead passes through the treatment protocol beginning with the safest treatment first and progressing until the patient's needs are met. The treatments are tailored to the patient to work on demand, effectively, with minimal side-effects, rapidly, and conveniently.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 2 illustrates the mechanism of ejaculation including the inhibitory effect of serotonins on ejaculation.

DETAILED DESCRIPTION OF ILLUSTRATIVE EMBODIMENTS

Figure 1A:
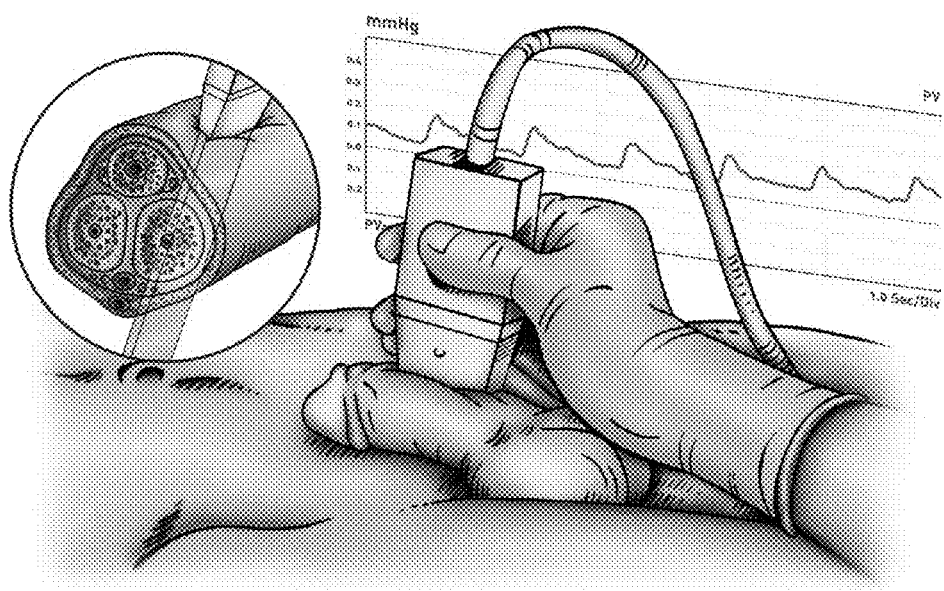
FIG. 1A illustrates an Eco-Doppler machine which is used to measure blood flow through the cavernosal artery of the penis.

Certain specific details are set forth in the following description with respect to FIGS. 1-3 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

The invention relates to a treatment protocol for primary premature ejaculation that provides treatment options for a patient that progress from the least effective/lowest side-effect profile to the highest effective/highest side-effect profile. The treatment protocol includes the gathering of information about the patient in order to distinguish primary premature ejaculation from secondary premature ejaculation and then selection of the targeted treatment options that progress from least to most effective with a consideration of the side-effect profile for each treatment.

Primarily due to the problem of under-reporting noted above, the treatment protocol in accordance with the invention incorporates two diagnostic tests to provide a tangible parameter with regard to the organic side of the disease and to assist with distinguishing secondary premature ejaculation from primary premature ejaculation.

Questionnaires

The two questionnaires below help distinguish primary from secondary premature ejaculation and the severity of secondary premature ejaculation.

1. Differentiating between primary and secondary premature ejaculation

If the answer is yes to (1) and/or (2) then a clinical diagnosis of secondary premature ejaculation is made and this is treated as erectile dysfunction. If the answer is negative to both questions or unclear, then the remainder of the questionnaire should be followed and the diagnostic tests performed as described below.

1. Are your erections as strong and lasting as they used to be before penetration?

2. Did you have control and then lose control when you develop an erection problem?

2. Verification of primary premature ejaculation and assessment of its severity

Assuming that the preliminary diagnosis is primary premature ejaculation, the following questions may be asked to further verify the presence of primary premature ejaculation:

| Primary Premature Ejaculation | |
|---|---|
| Date of onset? | Usually from first sexual encounter |
| Cultural, religious, educational factors? | Guilt from sexual relations or masturbation Strict religious beliefs Delayed or inadequate sexual education |
| Characteristics of sexual encounters? | Always has premature ejaculation although may perform better on occasions with use of alcohol or drugs |
| Duration after penetration? (timing with stopwatch if possible) | Usually seconds to several minutes. May ejaculate before penetration |
| Treatments tried and results? | Usually will have tried masturbation exercises, stop-start techniques or anesthetic creams with poor results |
| Effect on patient or his partner? | Patient and or partner avoid sexual relations, infertility in severe cases, relationship problems, lack of sexual enjoyment, depression, low self-esteem |

Positive responses to the above questions not only further verify the presence of primary premature ejaculation, but also help ascertain its severity and the eligibility of the patient to be treated according to the treatment protocol described below.

Diagnostic Tests

Two diagnostic tests are performed to help confirm the presence of primary premature ejaculation or to differentiate between primary and secondary premature ejaculation when questionnaires provide dubious results.

1. Eco-Doppler

Eco-Doppler is an excellent and highly accurate means of assessing patients with erectile dysfunction (Bookstein J. J., Valji K., Parsons L. et al., "Penile pharmacocavernosography and cavernosometry in the evaluation of impotence," J Urol. 1987; 137(2):333-7). An Eco-Doppler procedure may be performed to exclude erectile dysfunction and confirm primary premature ejaculation especially when the clinical history does not yield conclusive results. As illustrated in FIG. 1A, An Eco-Doppler procedure includes placing an ultrasonic instrument placed over the cavernosal artery of the penis to measure blood flow. A reduction in blood flow from the norm (usually 20 cm/second) would tend to suggest secondary premature ejaculation.

2. Penile Biothesiometry

Figure 1B:
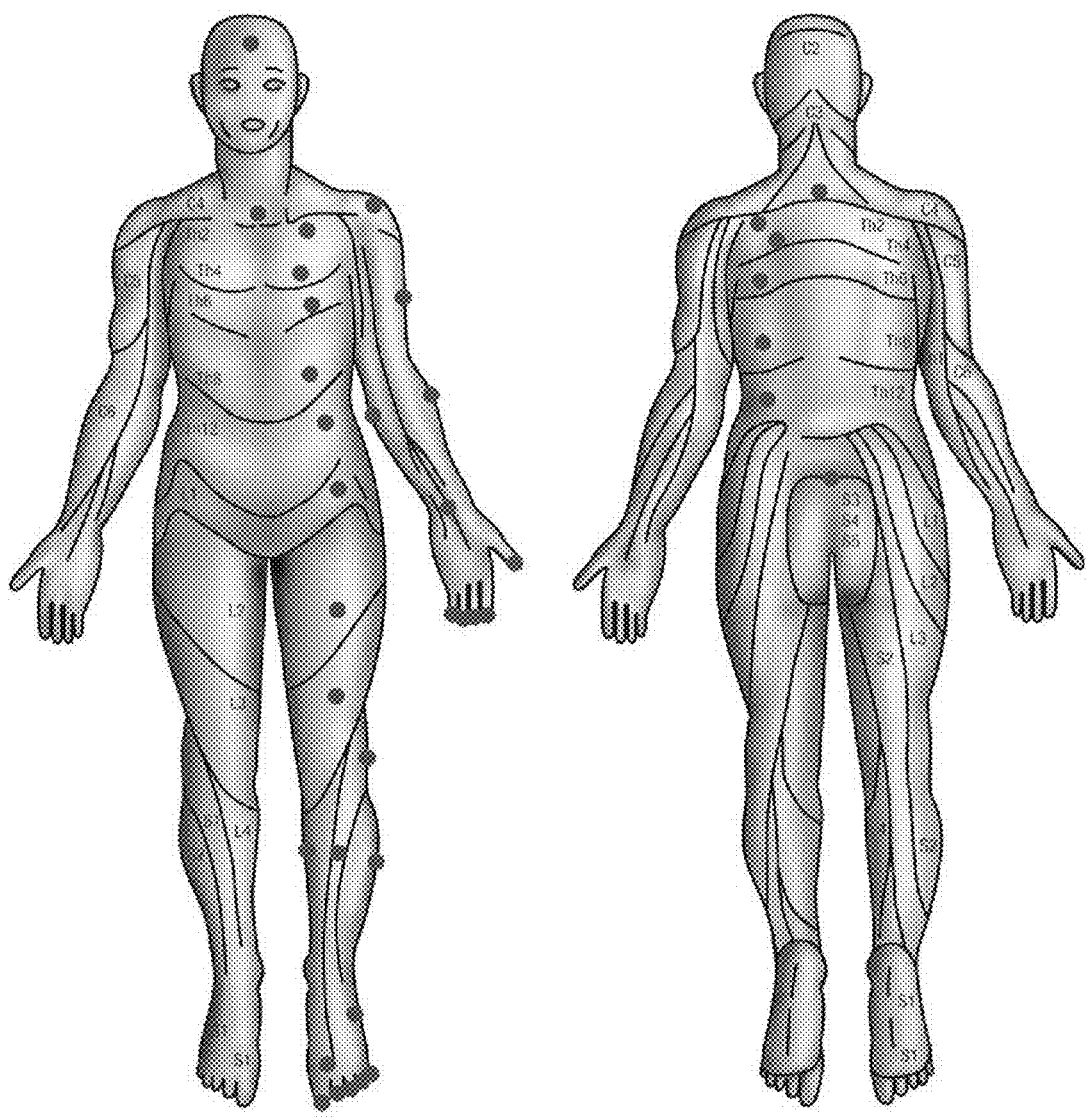
FIG. 1B illustrates a biothesiometry test that uses electromagnetic vibration to evaluate sensitivity and nerve function in the glans and shaft of the penis.

Penile biothesiometry can be used to confirm a penile hypersensitivity providing further implications for an organic basis of premature ejaculation (Xin Z. C., Chung W. S. et al., "Penile sensitivity in patients with primary premature ejaculation," J Urol. 1996; 156:979-81). FIG. 1B illustrates a biothesiometry test that uses electromagnetic vibration to evaluate sensitivity and nerve function in the glans and shaft of the penis. A patient with premature ejaculation will usually detect vibrations at a lower frequency in these areas. A positive test further confirms a diagnosis of primary premature ejaculation.

Treatment Options for Premature Ejaculation

As premature ejaculation is not a life-threatening condition, the chosen treatment(s) should be as safe and non-invasive as possible (Semans J. H., "Premature ejaculation: a new approach," South Med J. 1956; 49:353-8). Listing the treatment options reveals a clean correlation between the effectiveness of the treatment and its side-effect profile. The more effective the treatment, the greater the level of invasiveness and degree of side-effects. All treatment options should be explained clearly to the patient before the final protocol is embarked upon.

In accordance with the treatment protocol of the invention, the following treatment options are listed from least invasive/lowest side-effect profile to most invasive/highest side-effect profile. This approach coincides with least to most effective.

1. Applied Behavioral Techniques

The following applied behavior techniques have been used in the art. As they do not involve medications, they are very low risk and have essentially no side-effects. However, these techniques are not particularly effective for many patients.

The "stop-start" technique is the oldest therapy available and prolongs the neuromuscular reflex responsible for ejaculation. Intercourse is initiated slowly and the man informs his partner to stop genital stimulation just before the peak of arousal. This cycle is repeated as necessary. On the other hand, the "squeeze technique," developed by Masters and Johnson, involves engaging in sexual intercourse and withdrawing seconds before the point of climax. The female partner is then instructed to firmly squeeze the head of the penis for five seconds. Unfortunately, clinical experience suggests that the success of these two techniques is poor and that these techniques are abandoned relatively soon, resulting in further frustration to both the patient and partner. Moreover, it has been reported that such techniques are considered by many to be unhelpful in resolving relationship issues as they are "intrusive, mechanical and may fracture a normal love/lust act, relationship and spontaneity" (Palmer et al., "Premature Ejaculation: A Clinical Update," Med. J. Aust. 2008; 188(11); pp. 662-6).

2. Topical Anesthetics

Topical preparations are used to reduce glans penis sensitivity and hence delay ejaculation. They are essentially lignocaine based preparations in the form of creams or aerosols and are applied to the glans of the penis 20 minutes or so before intercourse. In a randomized placebo-controlled study of this treatment, latency times showed only a slight increase (Busato W., Galindo C. C., "Topical Anaesthetic use for treating premature ejaculation: a double-blind randomised, placebo-controlled study," BJU Int. 2004; 93:1018-21). Side effects include significant penile hypoanesthesia leading to reduced pleasure and loss of erection. Local symptoms of irritation and burning are also noted (Choi H. K., Jung G. W. et al., "Clinical study of SS-cream in patients with lifelong premature ejaculation," Urology, 2000; 55:257-61). Transvaginal absorption leading to female anorgasmia also is a known complication (Berkovitch M., Keresteci A. G. & Koren G., "Efficacy of prilocaine-lidocaine cream in the treatment of premature ejaculation," J Urol. 1995; 154:1360-1).

Applied behavioral techniques and topical anesthetics are two treatments that are often referred to as "traditional methods." These treatment methods prevailed until more modern methods using medication became available. Due to the lack of scientific data to support them and their unpredictable and disappointing results, they are mentioned here from a historical prospective only and have been excluded from the final treatment protocol of the invention as described below.

3. Pharmacotherapy for Premature Ejaculation

The drugs for treating premature ejaculation fall under three broad categories: serotonergic drugs, tramadol and intracavernous Alprostadil injections. The first two can be used regularly or on demand, and the latter on demand only.

Serotonergic Drugs

The introduction of the serotonergic drugs Clomipramine, Paroxetine, Sertraline, Fluoxetine and Citalopram (off-label uses) has revolutionized the approach to, and the treatment of premature ejaculation (Medicine Today, March 2010, Volume 11, Number 3, "Diagnosing and management premature ejaculation," page 40). These drugs act by increasing the amount of available serotonin resulting in ejaculatory delay due to serotonin's inhibitory effect on ejaculation (Waldinger M. D., Berendsen H. H. et al., "Premature ejaculation and serotonergic antidepressants-induced delayed ejaculation: the involvement of the serotonergic system," Behav Brain Res., 1998; 92:111-8). As shown in FIG. 2, serotonergic drugs stop the uptake of serotonin to thus control the rhythmic contractions of the pelvic floor muscles and mask mucosal sensor receptors in the penis, thereby inhibiting ejaculation. In the inventors' clinical experience, the drug of choice for the treatment of premature ejaculation needs to have the following characteristics to ensure maximum patient acceptance and satisfaction:

a. A drug with the lowest side-effect profile is desired as premature ejaculation is not a life-threatening condition and patients will usually only tolerate minor side-effects.

b. A drug that can be taken on an on demand basis rather than continuously.

c. A drug with a rapid onset of action.

Clomipramine

The oral administration of Clomipramine (brand name Anafranil) to treat men with premature ejaculation on an on-demand basis is well described. Clomipramine has been approved for the treatment of obsessive compulsive disorder, major depressive disorder, panic disorder, body dysmorphic disorder, and other mental and emotional disorders. Clomipramine has been shown to have a significant effect at delaying ejaculation but with a common side-effect profile including blurred vision, nausea, dry mouth, fatigue, dizziness, headache, loss of libido, and others. See, for example, Strassberg et al., "Clomipramine in the treatment of rapid (premature) ejaculation," J. Sex Marital Ther., 1999; 25(2); pp. 89-101; and Kim et al., "Efficacy and safety of fluoxetine, sertraline and clomipramine in patients with premature ejaculation: a double-blind, placebo controlled study," J. Urol. 1998; 159(2); pp. 425-7. For on-demand use, patients needed to take Clomipramine some 3-4 hours before sexual relations, a circumstance far from ideal! The challenge, therefore, is to find a more rapid method of delivery and absorption and a way to minimize the dosage and consequent side-effects. To do this, the inventor chose to hasten delivery and reduce the dose by opting for the sublingual (under the tongue) and intranasal (in the nose) routes. Medication administered through these routes is absorbed directly into the bloodstream, resulting in a more rapid onset of action and a lower required dose. Keeping the dose of Clomipramine as low as possible is particularly important as the adverse events and beneficial effects of Clomipramine appear to be dose related (Althof S. E., Levine S. B. et al., "A double-blind crossover trial of clomipramine for rapid ejaculation in 15 couples," J Clin Psychiatry, 1995; 56(9):402-7).

As the dosage of Clomipramine administered via the sublingual and nasal routes is well below the therapeutic range, side-effects are rare and include mostly local nasal irritation or taste disturbance. The troche holds the maximum dose and can cause a small but significant degree of nausea, hence the addition of small amounts of Metoclopramide, a common anti-nauseant. Table 1 below illustrates sample dosages and the time for onset of action.

TABLE 1

Formulation of clomipramine on demand used to treat primary premature ejaculation

| Solution of clomipramine | Delivery | Dosage | Onset of Action |
|---|---|---|---|
| clomipramine salt in aqueous formulation 40 mg/ml with nozzle dispensing .1 ml increments | Sublingual | ↓80 kg*<br>1-2 sprays (4-8 mg)<br>↑80 kg<br>2-3 sprays 8-12 mg) | 20-30 minutes |
| clomipramine salt in aqueous formulation 40 mg/ml with nozzle dispensing .1 ml increments | Intranasal | ↓80 kg*<br>1-2 sprays (4-8 mg)<br>↑80 kg<br>2-3 sprays 8-12 mg) | 10-15 minutes |
| Troche of clomipramine salt and metoclopramide with lactose and partially hydrolysed gelatin | Buccal or sublingual | ↓80 kg†<br>20 mg + 2 or<br>40 mg + 4<br>↑80 kg<br>30 mg + 3 or<br>50 mg + 5<br>(clomipramine + metoclopramide) | 20-30 minutes |

*The need to weigh the patient is important as the dosage of clomipramine recommended depends to some extent on the patient's weight.
†Start at lower dose and increase as shown until respon e is acceptable.

Tramadol

Tramadol (brand name ConZip or Ryzolt) is an effective treatment for patients with premature ejaculation and represents a promising alternative to the currently use oral pharmacologic agents (Wong B. L. & Malde S., "The use of tramadol "on-demand" for premature ejaculation: a systematic review," Urology, 2013; 81(1):98-103. doi: 10.1016/j.u- rology.2012.08.037. Epub 2012 Oct. 24). Tramadol is an "on demand" treatment, a centrally acting opioid analgesic for treating moderate to severe pain, and a weak inhibitor of the re-uptake of serotonin. Its mechanism of action is illustrated in FIG. 2. Tramadol represents an alternative for those who cannot tolerate mainstream serotinergic drugs (Salem E. A., Wilson S. K. et al., "Tramadol HCL has promise in on-demand use to treat premature ejaculation," J Sex Med. 2008; 5(1):188-93).

Tramadol is included in the treatment protocol as it fits the category of an on-demand treatment and can be used sublingually for a rapid mode of action with few side-effects such as nausea, dizziness, dry mouth, and headache. As just noted, Tramadol is a recommended option for patients who cannot tolerate serotinergic drugs. Its position in the treatment protocol as the last oral option is due to the small but potential risk of addiction (Cossman M. et al., "Tolerance and safety of tramadol use. Results of international studies and data from drug surveillance," Drugs, 1997; 53 Suppl 2:50-62). For dosage specification and delivery methods and delay to the onset of action, see Table 2 below. Side-effects are dose related and include dizziness, headache, nausea, blurred vision and dry mouth. As with Clomipramine, using a troche as a vehicle enables direct absorption into the blood-stream resulting in a lower (sub-therapeutic) dose and a more rapid onset of action.

TABLE 2

On demand tramadol for the treatment of primary premature ejaculation

| On demand tramadol | Delivery | Dosage* | Onset of Action |
| --- | --- | --- | --- |
| Troche of tramadol salt combined with lactose and partially hydrolysed gelatin | Buccal | 10 mg 20 mg 30 mg | 20-40 minutes |

*Start at lower dose and increase shown to achieve desired effect.

Intracavernous Pharmacotherapy-Alprostadil

Intracavernous pharmacotherapy has been shown to improve the latency time in patients with premature ejaculation. See Fein, "Intracavernous medication for treatment of premature ejaculation," Urology, 1990; 35:301. This involves the injection of certain vasodilators into the corpus cavernosum of the penis to provoke an erection. This induced erection will not subside with ejaculation. It will continue until the circulating vasodilators are absorbed, the duration of which is usually 40-60 minutes and dose dependent. As there are several components and combinations of components, it is desired to find the safest and most effective drug. As these drugs are injected locally into the corpus cavernosum and are broken down locally, systemic side-effects are practically insignificant but there are local side-effects of some concern. The three most common vasoactive drugs are listed in Table 3 below together with their side-effects (Porst H., "The rationale for prostaglandin E1 in erectile failure: a survey of worldwide experience," J Urol. 1996; 155:802-15).

TABLE 3

Vasoactive drugs and their side effects

| Drug | No. Patiens (No. of publications) | Priapism (%) | Fibrosis (%) | Pain (%) | Liver Enzymes (%) |
| --- | --- | --- | --- | --- | --- |
| Papaverine | 1527 (15) | 7.1 | 5.7 | 4 | 1.6 |
| Pap./Phentol. | 2263 (22) | 7.8 | 12.4 | 11.6 | 5.4 |

TABLE 3-continued

Vasoactive drugs and their side effects

| Drug | No. Patiens (No. of publications) | Priapism (%) | Fibrosis (%) | Pain (%) | Liver Enzymes (%) |
| --- | --- | --- | --- | --- | --- |
| PGE (Alprostadil) | 2745 (10) | 0.36 | 0.8 | 7.2 | 0 |

The drugs listed in Table 3 include Papaverine, Phentolamine and PGE (Alprostadil). As a result of the reduced side-effects, and numerous other studies, Alprostadil, a synthetic prostaglandin, is the drug of choice for the treatment of premature ejaculation using Intracavernous Pharmacotherapy. It has the lowest rate of priapism, fibrosis or scarring of the penis, post injection pain and interference with the liver enzymes. Furthermore, Alpostradil is the only vasoilator approved by the FDA for intra-cavernosal use. The remaining vasodilators are prescribed "off-label." The dosing regime is outlined in Table 4, starting with the lowest dose and titrating upwards until a resultant erection of 40-60 minutes is achieved.

TABLE 4

Intercavernous pharamacotherapy (ICP) for primary premature ejaculation - dosages of Alprostadil

| Alprostadil | Delivery | Dosage* | Onset of Action |
| --- | --- | --- | --- |
| Alprostadil (Prostaglandin E.) dissolved in sterile normal saline Concentration 20 mcg/ml | Intracavernosal via injection | 5 mcg = .25 ml 10 mcg = .5 ml 20 mcg = 1 ml | 5-10 minutes |

*Start at lower dose and increase as shown to achieve desired effect.

Treatment Protocol

As will be appreciated from the above description, the diagnosis and treatment of premature ejaculation is multi-faceted and complex. The treatment protocol of the invention is designed to introduce a standardized process that a clinician may follow to achieve the safest and most effective treatments available in the shortest number of steps. Given the fact that it is now well-known that premature ejaculation has a strong organic (physiological) basis, the treatment protocol has been adapted accordingly. In particular, the treatment protocol is designed to work on an "on-demand" basis, be effective but with minimalized secondary consequences, work rapidly, and be convenient in terms of usage (i.e.—use the lowest dose possible).

Figure 3:
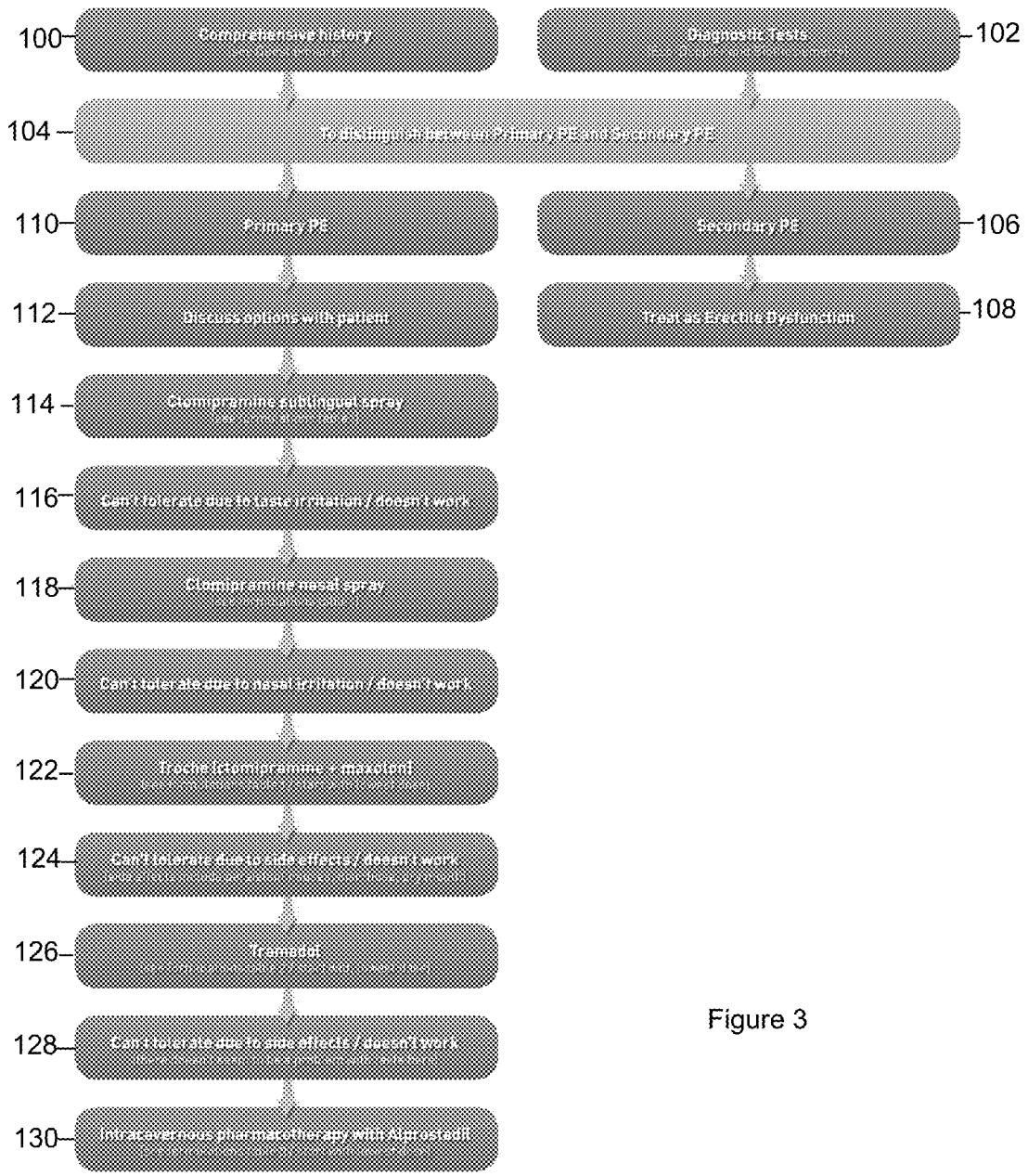
FIG. 3 illustrates the treatment protocol of an exemplary embodiment of the invention.

FIG. 3 captures the techniques discussed above into a standardized treatment protocol of an exemplary embodiment of the invention. As illustrated, the treatment protocol starts with the traditional approaches of using questionnaires to establish a comprehensive history of the patient's medical condition and sexual history at 100. Diagnostic tests, such as Eco-Doppler and Biothesiometry discussed above, may also be used at 102 to gather the data needed to distinguish at 104 between primary premature ejaculation and secondary premature ejaculation. If secondary premature ejaculation 106 is diagnosed, then the patient is treated for erectile dysfunction. As noted above, a number of techniques for treating erectile dysfunction may be used, including those described in U.S. Pat. No. 7,405,222 to Sallis et al.

On the other hand, if primary premature ejaculation 110 is diagnosed, the physician optionally discusses the treatment options (based on, for example, the severity of the disease) with the patient at 112, including the pharmacological options and the attendant side-effects. The patient is then started at 114 with a Clomipramine sublingual spray including a clomipramine salt in aqueous formulation of 40 mg/ml for nozzle dispensing in 0.1 ml increments. For patients weighing less than 80 kg, 1-2 sprays (4-8 mg) are used, and for patients weighing more than 80 kg, 2-3 sprays (8-12 mg) are used. In general, the amount of spray increases as the patient's weight increases. As indicated in Table 1, such a formulation should start working in 20-30 minutes.

If the patient cannot tolerate the Clomipramine sublingual spray at 116 due to bad taste or irritation, or if the Clomipramine sublingual spray does not work, then a Clomipramine nasal spray is tried at 118 for the same formulation, as shown in Table 1. As before, for patients weighing less than 80 kg, 1-2 sprays (4-8 mg) are used, and for patients weighing more than 80 kg, 2-3 sprays (8-12 mg) are used. As indicated in Table 1, such a formulation should start working in 10-15 minutes.

If the patient cannot tolerate the Clomipramine nasal spray at 120 due to nasal irritation, or if the Clomipramine nasal spray does not work, then a troche of Clomipramine salt plus metoclopramide with lactose and partially hydrolyzed gelatin (maxolon) is delivered buccally or sublingually to the patient at 122. As shown in Table 1, for patients weighing less than 80 kg, 20 mg clomipramine plus 2 mg metoclopramide or 40 mg clomipramine plus 4 mg metoclopramide are used, and for patients weighing more than 80 kg, 30 mg clomipramine plus 3 mg metoclopramide or 50 mg clomipramine plus 5 mg metoclopramide are used, starting at a lower dose and increasing until the response is acceptable. Of course, other dosage intervals may be used as deemed appropriate. As indicated in Table 1, such formulations should start working in 20-30 minutes.

If the patient cannot tolerate the troche at 124 due to side-effects, or if the troche does not work, then an on demand formulation of tramadol is provided to the patient buccally. As illustrated in Table 2, the tramadol is delivered at 126 as a troche of tramadol salt combined with lactose and partially hydrolyzed gelatin at doses starting at lower doses such as 10 mg and progressing to higher doses such as 20 mg and 30 mg, as needed, to achieve the desired effect. Of course, other dosage intervals may be uses as deemed appropriate. As indicated in Table 2, such formulations should start working in 20-40 minutes.

Finally, if the patient cannot tolerate the troche of tramadol at 128 due to side-effects, or if the troche of tramadol does not work, then the patient is treated with intracavernous pharmacotherapy of Alprostadil at 130. As illustrated in Table 4, the Alprostadil (prostaglandin $E_1$) is dissolved in a sterile normal saline at a concentration of, for example, 20 mcg/ml, for intracavernosal injection directly into the penis. The doses start at lower doses such as 5 mcg=0.25 ml and progress to higher doses such as 10 mcg=0.5 ml and 20 mcg=1 ml, as needed, to achieve the desired effect. Of course, other dosage intervals may be uses as deemed appropriate. As indicated in Table 4, such formulations should start working in 5-10 minutes.

It will be appreciated by those skilled in the art that the treatment protocol laid out in FIG. 3 progresses to the safest and most effective methodology in the shortest number of steps in that individual patients progress through the protocol only until they get satisfactory results. They start with the safest treatment available and progress through the protocol until their needs are met. The treatments are thus tailored to the patient to work on demand, effectively, with minimal side-effects, rapidly, and conveniently.

Those skilled in the art also will readily appreciate that many additional modifications are possible in the exemplary embodiment without materially departing from the novel teachings and advantages of the invention. Accordingly, any such modifications are intended to be included within the scope of this invention as defined by the following exemplary claims.

What is claimed:

1. A method of treating primary premature ejaculation in a male mammal, comprising the steps of:
   assessing the condition of the male to establish that the male has primary premature ejaculation as opposed to secondary premature ejaculation; and
   if the male is diagnosed as having primary premature ejaculation, identifying a treatment protocol that progresses to a safest and most effective methodology in a shortest number of steps by progressing the male through at least two of the following steps in sequence until a satisfactory delay of ejaculation is achieved:
   applying a clomipramine sublingual spray in an amount effective to delay ejaculation by the male,
   applying a clomipramine nasal spray in an amount effective to delay ejaculation by the male,
   applying a troche of clomipramine buccally or sublingually in an amount effective to delay ejaculation by the male,
   applying tramadol buccally in an amount effective to delay ejaculation by the male, and injecting a vasodilator into a corpus cavernosum of the male's penis in an amount sufficient to provoke a lasting erection.

2. The method of claim 1, wherein assessing the condition of the male includes using questionnaires to a establish a comprehensive history of the patient's medical condition and sexual history.

3. The method of claim 1, wherein assessing the condition of the male includes applying diagnostic test to the male including Eco-Doppler testing to measure blood flow of the penis and biothesiometry studies to determine the sensitivity of the nerves of the penis.

4. The method of claim 1, wherein applying the clomipramine sublingual spray comprises applying an aqueous formulation of clomipramine salt sublingually in a dosage from 4-12 mg based on the male's weight.

5. The method of claim 1, wherein applying the clomipramine nasal spray comprises applying an aqueous formulation of clomipramine salt nasally in a dosage from 4-12 mg based on the male's weight.

6. The method of claim 1, wherein applying the troche of clomipramine comprises applying a combination of clomipramine salt and an amount of an anti-nauseant sufficient to suppress nausea buccally or sublingually in a dosage of 20 mg of clomipramine and 2 mg of the anti-nauseant, determining if an effective delay of ejaculation is achieved, and increasing the dosage of clomipramine and anti-nauseant up to 50 mg and 5 mg, respectively, until an effective delay of ejaculation is achieved.

7. The method of claim 1, wherein applying tramadol buccally in an amount effective to delay ejaculation by the male comprises applying a troche of tramadol salt buccally in a dosage of 10 mg of tramadol, determining if an effective delay of ejaculation is achieved, and increasing the dosage of tramadol up to 30 mg until an effective delay of ejaculation is achieved.

8. The method of claim 1, wherein injecting a vasodilator into a corpus cavernosum of the male's penis comprises injecting a solution of Alprostadil in a dosage of 0.25 ml of Alprostadil, determining if an effective delay of ejaculation is achieved, and increasing the dosage of Alprostadil up to 1 ml until an effective delay of ejaculation is achieved.

* * * * *